(12) United States Patent
Mori et al.

(10) Patent No.: US 8,786,692 B2
(45) Date of Patent: Jul. 22, 2014

(54) IMAGE PROCESSING DEVICE AND ELECTRONIC APPARATUS

(75) Inventors: Ichiro Mori, Chiba (JP); Hidetoshi Kabasawa, Saitama (JP)

(73) Assignee: Sony Corporation, Tokyo (JP)

( * ) Notice: Subject to any disclaimer, the term of this patent is extended or adjusted under 35 U.S.C. 154(b) by 528 days.

(21) Appl. No.: 12/835,316

(22) Filed: Jul. 13, 2010

(65) Prior Publication Data

US 2011/0037843 A1    Feb. 17, 2011

(30) Foreign Application Priority Data

Aug. 12, 2009  (JP) .................................. 2009-187048

(51) Int. Cl.
*H04N 7/18* (2006.01)

(52) U.S. Cl.
USPC .......................................................... 348/77

(58) Field of Classification Search
CPC ... H04N 7/18; G06K 9/2018; G06K 9/00255; G06K 9/00362; G06T 7/0097
USPC .......................................................... 348/77
IPC .......................................................... H04N 7/18
See application file for complete search history.

(56) References Cited

U.S. PATENT DOCUMENTS

| | | | | |
|---|---|---|---|---|
| 5,903,006 A * | 5/1999 | Kiuchi et al. | ............ | 250/339.12 |
| 6,471,464 B1 * | 10/2002 | Fay et al. | ....................... | 414/783 |
| 7,224,483 B2 * | 5/2007 | Hanabusa et al. | | |
| 8,107,706 B2 * | 1/2012 | Saijo | .............................. | 382/128 |
| 2002/0030445 A1 * | 3/2002 | Fukasawa | ...................... | 313/512 |
| 2003/0080193 A1 * | 5/2003 | Ryan et al. | ..................... | 235/491 |
| 2005/0049468 A1 * | 3/2005 | Carlson et al. | ................ | 600/323 |
| 2006/0034537 A1 * | 2/2006 | Masaki | .......................... | 382/254 |
| 2008/0177185 A1 * | 7/2008 | Nakao et al. | ................... | 600/476 |
| 2009/0310827 A1 * | 12/2009 | Einighammer et al. | ....... | 382/115 |

FOREIGN PATENT DOCUMENTS

| | | |
|---|---|---|
| JP | 4-52877 A | 2/1992 |
| JP | 2004-164483 A | 6/2004 |
| JP | 2004-310695 A | 11/2004 |
| JP | 2006-47067 A | 2/2006 |
| JP | 2007-233290 A | 9/2007 |
| JP | 2008-182360 A | 8/2008 |

OTHER PUBLICATIONS

SwissRanger SR3000 and First Experiences based on Miniaturized 3D-TOF Cameras, Thierry Oggier et al., 1st Range Imaging Research Day, ETH Zurich, 2005.*
Japanese Office Action Issued Feb. 5, 2013 in Patent Application No. 2009-187048.

* cited by examiner

*Primary Examiner* — Jay Patel
*Assistant Examiner* — Francis G Geroleo
(74) *Attorney, Agent, or Firm* — Oblon, Spivak, McClelland, Maier & Neustadt, L.L.P.

(57) ABSTRACT

An image processing device for detecting a skin area representing the skin of a person in an image obtained by imaging an object, includes: a first light source section emitting light having a first wavelength; a second light source section emitting light having a second wavelength different from the first wavelength; an imaging section imaging an object illuminated by the light having the first wavelength and imaging an object illuminated by the light having the second wavelength; a detecting section detecting a skin area in either first or second image respectively obtained by imaging the object illuminated by the light having the first or second wavelength based on the first and the second images; and a substrate on which the first and second light emitting sections are disposed integrally with the imaging section and the detecting section in such positions that the light emitting sections are symmetric about the imaging section.

15 Claims, 10 Drawing Sheets

IMAGE PROCESSING DEVICE AND ELECTRONIC APPARATUS

BACKGROUND OF THE INVENTION

1. Field of the Invention

The present invention relates to an image processing device and an electronic apparatus. More particularly, the invention relates to an image processing device and electronic apparatus which are suitable for detecting the shape of a hand of a person or the like, for example, in an image obtained by imaging the object.

2. Description of the Related Art

In the related art, there are skin recognition systems which detect (recognize) a skin area representing the skin of a person in an image obtained by imaging an object (for example, see Yasuhiro Suzuki et al. "Proposal on Skin Detection by Near Infrared Multi-Band", IEEJ Transactions C, No. 4, Volume 127, 2007, Japan (Non-Patent Document 1)).

FIG. 1 shows an exemplary configuration of a skin recognition system 1 according to the related art.

The skin recognition system 1 includes a light source section 21, a camera 22, and an image processing section 23.

The light source section 21 includes LEDs (light-emitting diodes) 21a each radiating (emitting) light having a wavelength $\lambda 1$ (e.g., near infrared light having a wavelength of 950 [nm]) which are represented by ten dots and LEDs 21b each radiating light having a wavelength $\lambda 2$ different from the wavelength $\lambda 1$ (e.g. near infrared light having a wavelength of 870 [nm]) which are represented by ten white circles.

The wavelengths $\lambda 1$ and $\lambda 2$ are combined such that the light of the wavelength $\lambda 1$ has a reflectance lower than that of the light of the wavelength $\lambda 2$ when those light rays are projected on human skin and such that the light rays having the respective wavelengths $\lambda 1$ and $\lambda 2$ are reflected at substantially the same reflectance when projected on an object other than human skin.

The LEDs 21a and the LEDs 21b are disposed so as to form a checkerboard pattern to emit light, for example, in an alternate manner.

The camera 22 images an object illuminated by the light of the wavelength $\lambda 1$ from the LEDs 21a and images an object illuminated by the light of the wavelength $\lambda 2$ from the LEDs 21b. The camera supplies each of the images thus imaged to the image processing section 23.

Specifically, the camera 22 receives a reflected light ray, i.e., the light of the wavelength $\lambda 1$ emitted by the LEDs 21a and reflected by an object and supplies a first image thus imaged to the image processing section 23. The camera 22 also receives another reflected light ray, i.e., the light of the wavelength $\lambda 2$ emitted by the LEDs 21b and reflected by the object and supplies a second image thus imaged to the image processing section 23.

The image processing section 23 calculates absolute differences between luminance values of pixels corresponding between the first and second images imaged by the camera 22 and detects a skin area in the first image (or the second image) based on the calculated absolute differences.

The reflectance at which the light of the wavelength $\lambda 1$ is reflected on human skin is lower than the reflectance at which the light of the wavelength $\lambda 2$ is reflected on human skin. Therefore, the luminance values of the pixels forming a skin area in the first image are relatively small, and the luminance values of the pixels forming the skin area in the second image are relatively great.

Therefore, absolute differences between the luminance values of the pixels forming the skin area in the first and second images have relatively great values. The reflectance at which the light of the wavelength $\lambda 1$ is reflected on an object other than human skin is substantially the same as the reflectance at which the light of the wavelength $\lambda 2$ is reflected on the object other than human skin. Therefore, the luminance values of the pixels forming an area of the first image other than the skin area are substantially the same as the luminance values of the pixels forming the area of the second image other than the skin area.

Thus, absolute differences between the luminance values of the pixels forming the area in the first and second images other than the skin area have relatively small values.

Therefore, the image processing section 23 of the skin recognition system 1 can detect an area of interest as a skin area, for example, when absolute differences as thus described have relatively great values.

Thus the skin recognition system 1 can detect the skin area of the first image based on the first and second images obtained by imaging the object.

For example, when the skin recognition system 1 is incorporated in a television receiver, a hand of a user can be detected, and a gesture of the user associated with a predetermined operation can be recognized from the result of the detection. Further, an operation such as changing a selected channel can be carried out based on what is recognized.

SUMMARY OF THE INVENTION

In the skin recognition system 1 according to the related art, the light source section 21, the camera 22, and the image processing section 23 are provided as separate components, which makes it difficult to incorporate the system into an electronic apparatus such as a television receiver.

In order to incorporate the skin recognition system 1 according to the related art in a television receiver and the like, a space must be provided in the receiver to accommodate the system, which necessitates a significant change in the shape of the television receiver and the like.

Under such circumstances, it is desirable to allow a skin recognition system to be made in such a small size that the system can be incorporated in an electronic apparatus such as a television receiver. Specifically, it is desirable to provide a skin recognition system having a small size while eliminating problems associated with illuminance and shadows (the problem of difficulty in providing sufficient illuminance and a sufficient light source when making the system small).

According to an embodiment of the invention, there is provided an image processing device for detecting a skin area representing the skin of a person in an image obtained by imaging an object, including a first light source section emitting light having a first wavelength, a second light source section emitting light having a second wavelength different from the first wavelength, an imaging section imaging an object illuminated by the light having the first wavelength and imaging an object illuminated by the light having the second wavelength, a detecting section detecting a skin area in either a first image obtained by imaging the object illuminated by the light having the first wavelength or a second image obtained by imaging the object illuminated by the light having the second wavelength, and a substrate on which the first and second light emitting sections are disposed integrally with the imaging section and the detecting section in such positions that the light emitting sections are symmetric about the imaging section.

The first and second light emitting sections may be disposed on a straight line on the substrate in such positions that they are symmetric about the imaging section which is located in the middle of the straight line.

The substrate may include a light source substrate on which the first and second light emitting sections are disposed on a straight line in such positions that they are symmetric about the imaging section which is located in the middle of the straight line and a processing substrate on which the imaging section and the detecting section are disposed.

The imaging section may be secured to the light source substrate such that the imaging section penetrates through the light source substrate in the normal direction thereof.

The light source substrate may be provided with a shield section for blocking light rays from the first and second light emitting sections which otherwise directly impinge on the imaging section.

The shield section may be formed from a metal.

A securing section may be further provided for securing the first and second light emitting sections in such positions that an imaging direction of the imaging section coincides with the light emitting directions of the first and second light emitting sections.

The securing sections may be formed from a metal.

A support section for supporting the substrate may be provided, and the securing section may be part of the support section.

A lens may be provided to allow light rays from the first and second light emitting sections to be radiated into an imaging range of the imaging section.

The lens may be a fly-eye lens or diffraction grating.

The first and second light emitting sections may be alternately disposed on the light source substrate in such positions that they are symmetric about the imaging section.

In the embodiment of the invention, the first and second light emitting sections are disposed on the substrate integrally with the imaging section and the detecting section in such positions that the light emitting sections are symmetric about the imaging section.

According to another embodiment of the invention, there is provided an electronic apparatus detecting a skin area representing the skin of a person in an image obtained by imaging an object and performing a process depending on the detected skin area, the apparatus including a first light source section emitting light having a first wavelength, a second light source section emitting light having a second wavelength different from the first wavelength, an imaging section imaging an object illuminated by the light having the first wavelength and imaging an object illuminated by the light having the second wavelength, a detecting section detecting a skin area in either a first image obtained by imaging the object illuminated by the light having the first wavelength or a second image obtained by imaging the object illuminated by the light having the second wavelength, a substrate on which the first and second light emitting sections are disposed integrally with the imaging section and the detecting section in such positions that the light emitting sections are symmetric about the imaging section, and a processing section performing a process according to the result of the detection performed by the detecting section.

In the embodiment, the first and second light emitting sections are disposed on the substrate integrally with the imaging section and the detecting section in such positions that the light emitting sections are symmetric about the imaging section, and a process is performed according to the result of the detection performed by the detecting section.

According to the embodiments of the invention, an image processing device for detecting the shape of a hand of a person or the like from an image obtained by imaging the object can be provided in such a small size that the device can be incorporated in an electronic apparatus.

DESCRIPTION OF PREFERRED EMBODIMENTS

A mode for implementing the invention (hereinafter referred to as embodiment) will be described below in the following order.

1. Embodiment (example of television receiver incorporating a skin recognition module)

2. Modification

1. Embodiment

[Front View of Television Receiver 41]

Figure 1:
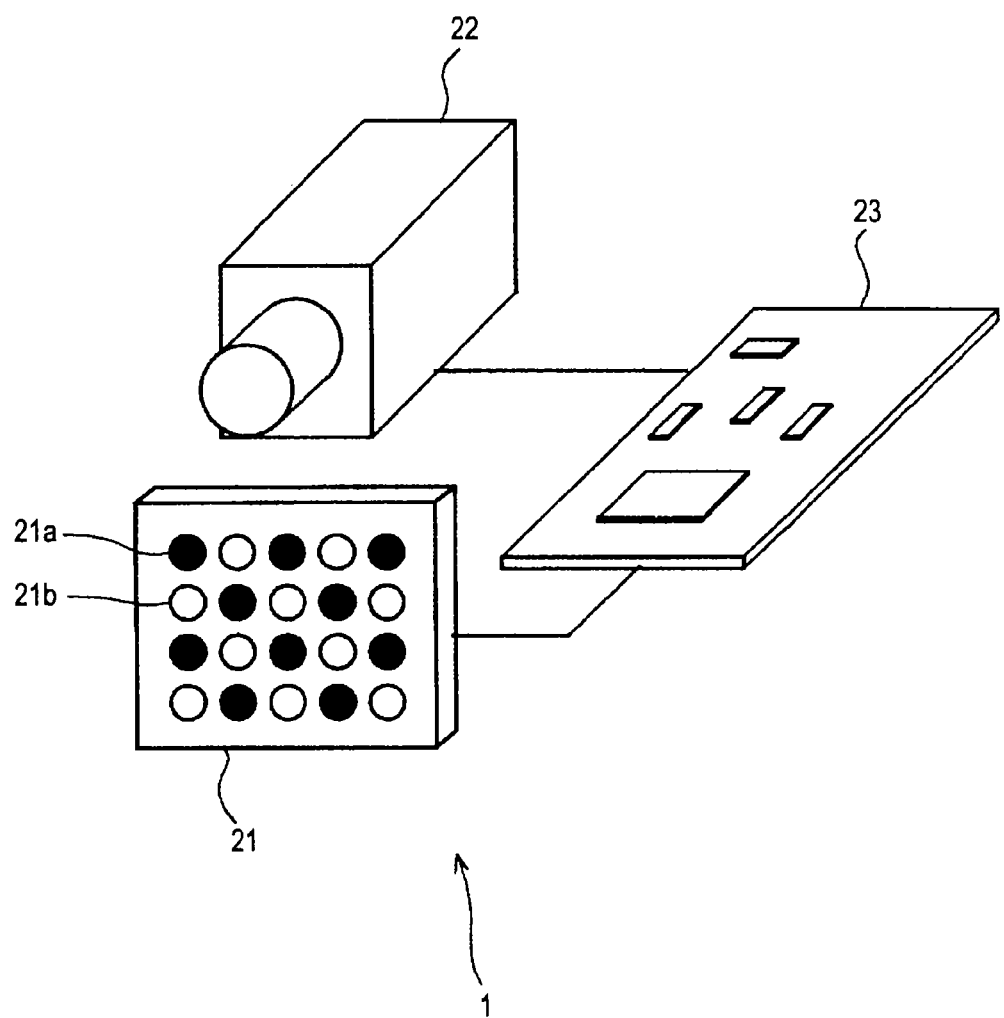
FIG. 1 is an illustration showing an exemplary configuration of a skin recognition system according to the related art.
Figure 2:
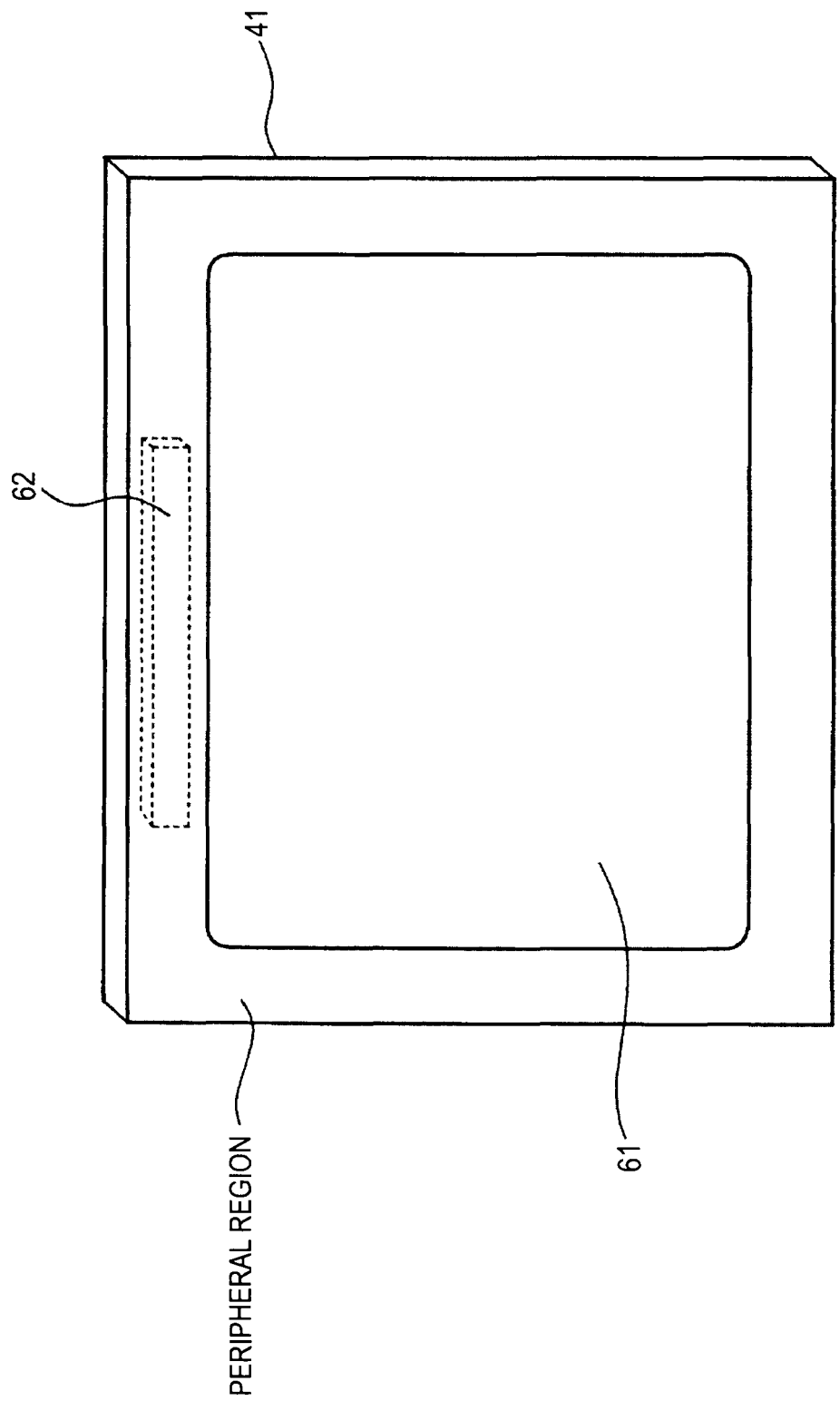
FIG. 2 is an illustration showing an example of a television receiver to which the invention is applied.

FIG. 2 shows a television receiver 41 to which the invention is applied.

The television receiver 41 includes a monitor 61, a skin recognition module 62, and a tuner (not shown) as primary features. The skin recognition module 62 is incorporated in a region around the periphery of the monitor 61 by making it compact such that it can be accommodated in the region around the periphery of the monitor 61 in the housing of the television receiver 41.

For example, the monitor 61 includes a liquid crystal display or organic EL (electro-luminescent) display, and the monitor displays images (television programs) associated with television broadcast signals.

The skin recognition module 62 images an object located in front of the monitor 61 (e.g., a user watching a television program) with a camera 84 (FIG. 3) incorporated therein. The skin recognition module 62 detects a skin area in an image obtained by the imaging operation and supplies the result of the detection to, for example, a tuner which is not shown.

For example, the tuner performs an operation of changing the channel displayed on the television receiver 41 as a process according to the detection result supplied from the skin recognition module 62.

[External View of Skin Recognition Module 62]

Figure 3:
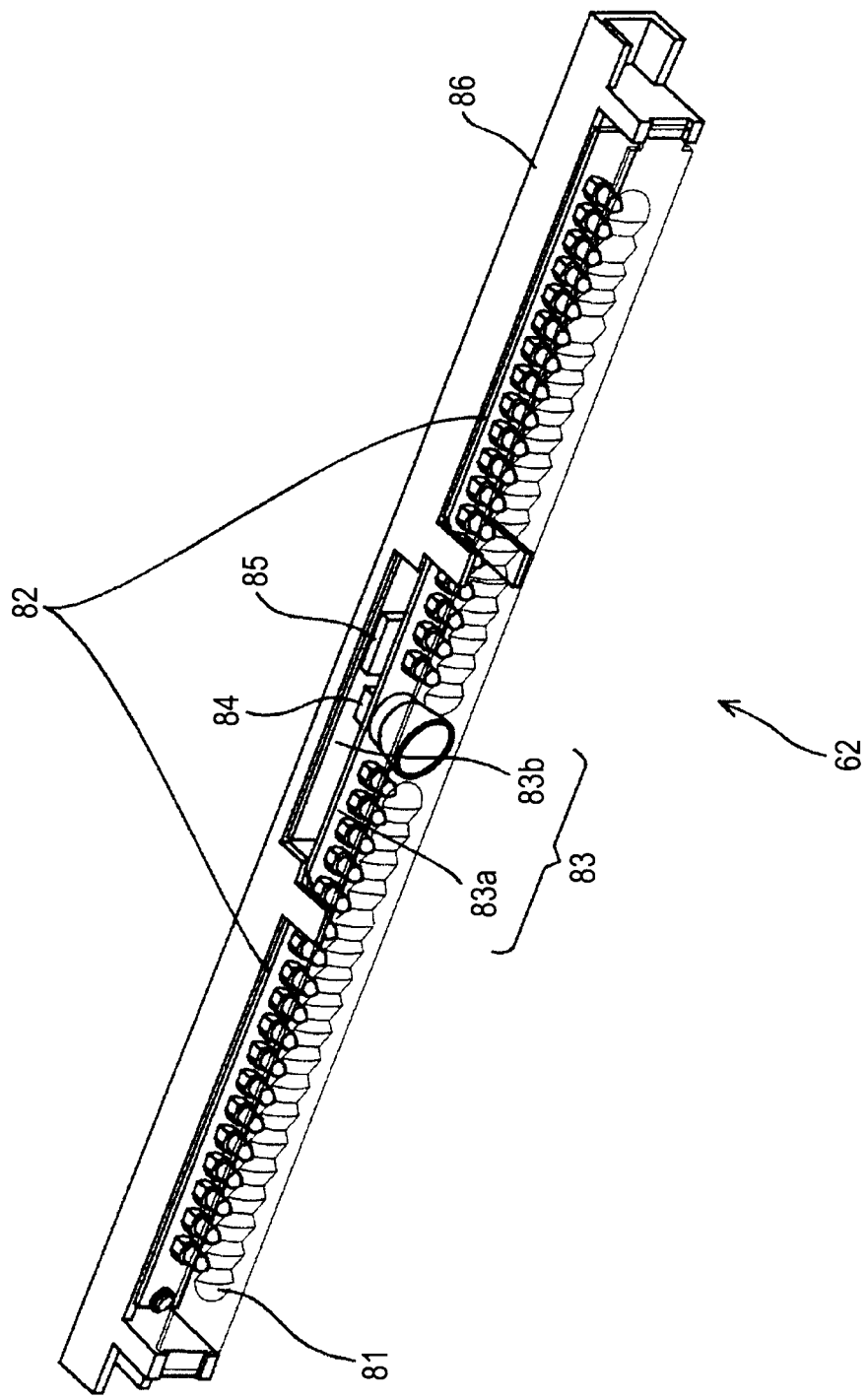
FIG. 3 is an illustration showing an example of a skin recognition module.

FIG. 3 shows an exemplary configuration of the skin recognition module 62.

The skin recognition module 62 includes a lens 81, a light source group 82, a substrate 83, a camera 84, an image processing section 85, and a support member 86.

The lens 81 collects light emitted by each of LEDs forming the light source group 82, corrects the collected light, for example, into a spot beam, and projects the beam on a two-dimensional plane that is an imaging range over which imaging is performed by the camera 84.

The light source group 82 is constituted by a set of LEDs radiating (emitting) light having a wavelength λ1 (near infrared light having a wavelength of, for example, 950 [nm]) and a set of LEDs radiating (emitting) light having a wavelength λ2 different from the wavelength λ1 (near infrared light having a wavelength of, for example, 870 [nm]). For example, the light source group 82 emits the light having the wavelength λ1 and the light having the wavelength λ2 alternately.

The substrate 83 includes a light source substrate 83a on which the light source group 82 is disposed and a processing substrate 83b on which the camera 84 and the image processing section 85 are disposed. The light source substrate 83a and the processing substrate 83b are provided as separate substrates.

The light source substrate 83a has an oblong rectangular shape, and the camera 84 is secured in the middle of the light source substrate 83a such that it extends through the substrate in the normal direction thereof. The LEDs forming the light source group 82 are disposed on a straight line on the light source substrate 83a, the array of LEDs being centered at the camera 84.

For example, the processing substrate 83b is a multi-layer substrate (which has, for example, four layers or six layers), and the substrate has an oblong rectangular shape like the light source substrate 83a. The processing substrate 83b is provided behind the light source substrate 83a. The camera 84 secured to the light source substrate 83a and the image processing section 85 are disposed on the processing substrate 83b.

For example, the camera 84 includes a CCD (charge coupled device) or a CMOS (complementary metal oxide semiconductor) image sensor. The camera images an object by illuminating the object with the light having the wavelength 21 and by illuminating the object with the light having the wavelength λ2 and supplies each of the images obtained by imaging the object to the image processing section 85.

Specifically, the camera 84 receives a reflected light ray, i.e., the light having the wavelength λ1 projected on and reflected by the object and supplies a first image obtained by imaging the object to the image processing section 85. The camera 84 receives another reflected light ray, i.e., the light having the wavelength λ2 projected on and reflected by the object and supplies a second image obtained by imaging the object to the image processing section 85.

For example, the image processing section 85 includes a DSP (digital signal processor) or the like, and the section detects an area representing the skin of a person from either the first or second image based on the first and second images from the camera 84.

The support member 86 supports the lens 81, the light source substrate 83a, and the processing substrate 83b.

In the present embodiment, as shown in FIG. 3, the light source group 82 is disposed on the light source substrate 83a, and the camera 84 and the image processing section 85 are disposed on the processing substrate 83b. The light source substrate 83a and the processing substrate 83b overlap each other.

Thus, the width of the skin recognition module 62 (the surface area of the light source substrate 83a) can be made smaller than that of the case where the light source group 82, the camera 84, and the image processing section 85 are disposed on one substrate (which may be, for example, the light source substrate 83a) instead of disposing the light source group 82 on a substrate and disposing the camera 84 and the image processing section 85 on a separate substrate.

In the present embodiment, since the light source substrate 83a and the processing substrate 83b are provided as separate substrates, the manufacturing cost of the light source substrate 83a and the processing substrate 83b can be kept lower than that required for forming the light source substrate 83a and the processing substrate 83b integrally.

Specifically, the light source substrate 83a has a relatively large size to obtain a light amount sufficient to illuminate an object. As described above, the processing substrate 83b includes a multi-layer substrate.

The manufacture of a substrate 83 formed by integrating a processing substrate 83b and a light source substrate 83a results in a higher manufacturing cost in general because of the complicatedness of the configuration.

In the present embodiment, the light source substrate 83a and the processing substrate 83b are provided as separate substrates to simplify the circuit structure. Thus, the manufacturing cost can be kept low.

Further, since the light source group 82 is uniformly disposed on a straight line (the LEDs are uniformly disposed over the entire width of the substrate), a uniform illuminance distribution can be easily achieved.

[Positional Relationship Between Light Source Group 82 and Camera 84]

Figure 4:
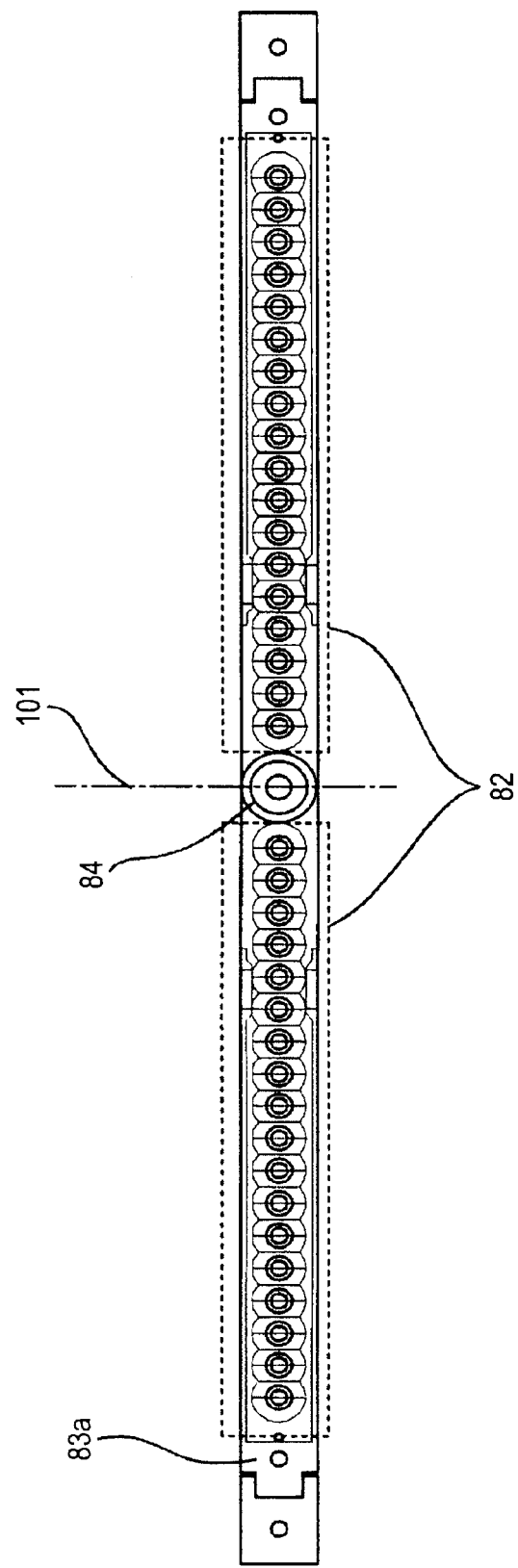
FIG. 4 is an illustration showing an example of disposition of a light source group and a camera.

FIG. 4 shows an example of a relationship between the light source group 82 and the camera 84.

As shown in FIG. 4, the camera 84 is secured at the center of the light source substrate 83a (in the middle of the substrate). Arrays of LEDs forming the light source group 82 are disposed on the light source substrate 83a to extend in the horizontal direction of the figure (on a straight line) in such positions that they are line-symmetric about the camera 84 secured to the substrate (an axis 101).

In the present embodiment, as shown in FIG. 4, the camera 84 is secured in the middle of the light source substrate 83a. Therefore, when a user makes a gesture in front of the television receiver 41 (the skin recognition module 62), the user making a gesture can be imaged in the frontal direction.

Therefore, a hand or the like of the user can be imaged by the camera 84 without being hidden by the body or the like of the user him- or herself. Thus, the skin recognition module 62 (image processing section 85) can accurately capture the motion or the like of the user's hand from first and second images obtained by imaging the user.

[Positional Relationship Between LED 121 and Lens 81]

Figure 5:
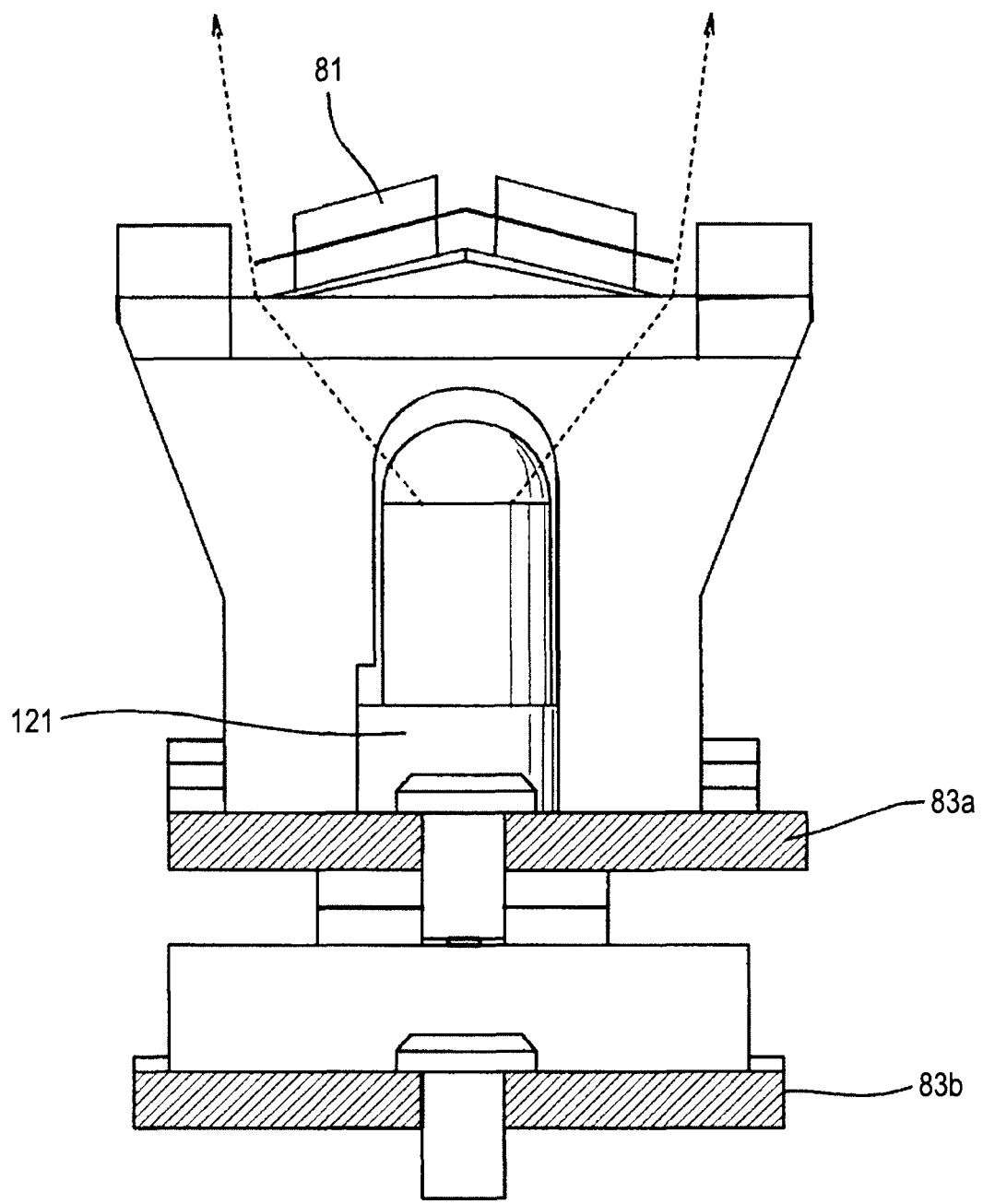
FIG. 5 is an illustration showing an example of disposition of LEDs forming the light source group and a lens.

FIG. 5 shows an example of a positional relationship between an LED 121 forming part of the light source group 82 and a lens 81.

As shown in FIG. 5, a lens 81 is disposed in front of each LED 121 forming part of the light source group 82.

As shown in FIG. 5, the lens 81 refracts light (divergent light) from the LED 121 to adjust (correct) the range illuminated by the LED 121 (illuminance distribution).

Figure 6:
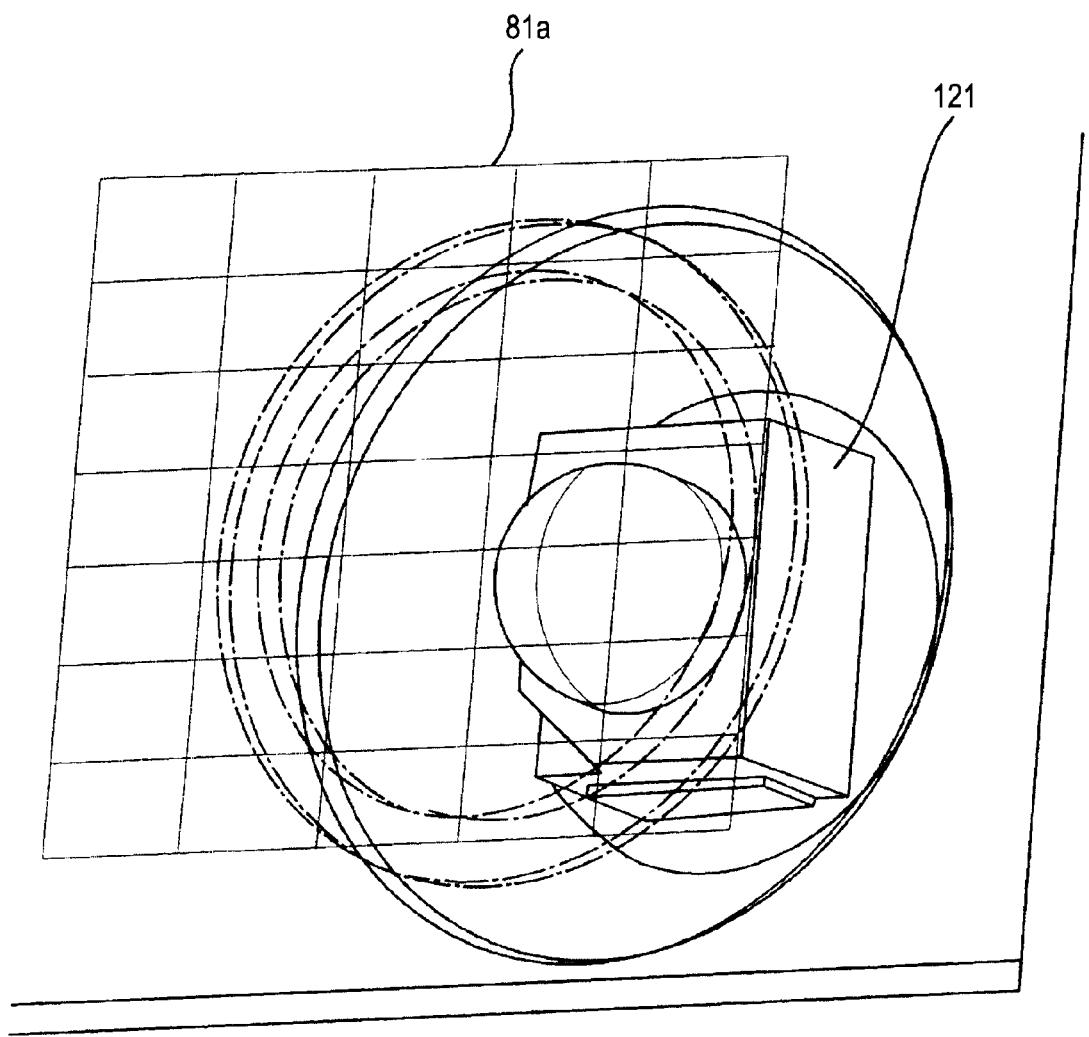
FIG. 6 is an illustration showing an example of a fly-eye lens.

For example, the lens 81 corrects the range illuminated by the LED 121 by narrowing the range (the range is corrected to an illumination range in the form of a spot narrower than the imaging range of the camera 84). As a result, even when the quantity of light from the LED 121 illuminating an object to be imaged is insufficient, the imaging range of the camera 84 is illuminated by a sufficient quantity of light. A fly-eye lens 81a as shown in FIG. 6 or a diffraction grating may be used as the lens 81.

When an object to be imaged can be illuminated by a sufficient quantity of light from the LED 121 alone, a configuration employing no lens 81 may be used.

In the present embodiment, since the lens 81 is provided in front of the LED 121 as shown in FIG. 5, the light from the LED 121 is (substantially entirely) radiated into the imaging range. Therefore, when compared to a case wherein light is radiated from the LED 121 as divergent light without correcting the same, the quantity of light from the LED 121 radiated out of the imaging range can be kept small to suppress loss of illumination light to illuminate an object residing in the imaging range.

Since the suppression of loss of illumination light allows the object to be efficiently illuminated by the light from the LEDs 121, the number of LEDs 121 can be smaller than the quantity required when, for example, the light from the LEDs 121 is not corrected by the lenses 81 or the like.

In the present embodiment, since the number of LEDs 121 can be kept small, the power consumption of the light source group 82 can be suppressed, and the skin recognition module 62 can be made compact.

[Example of Light Source Group 82]

Figure 7:
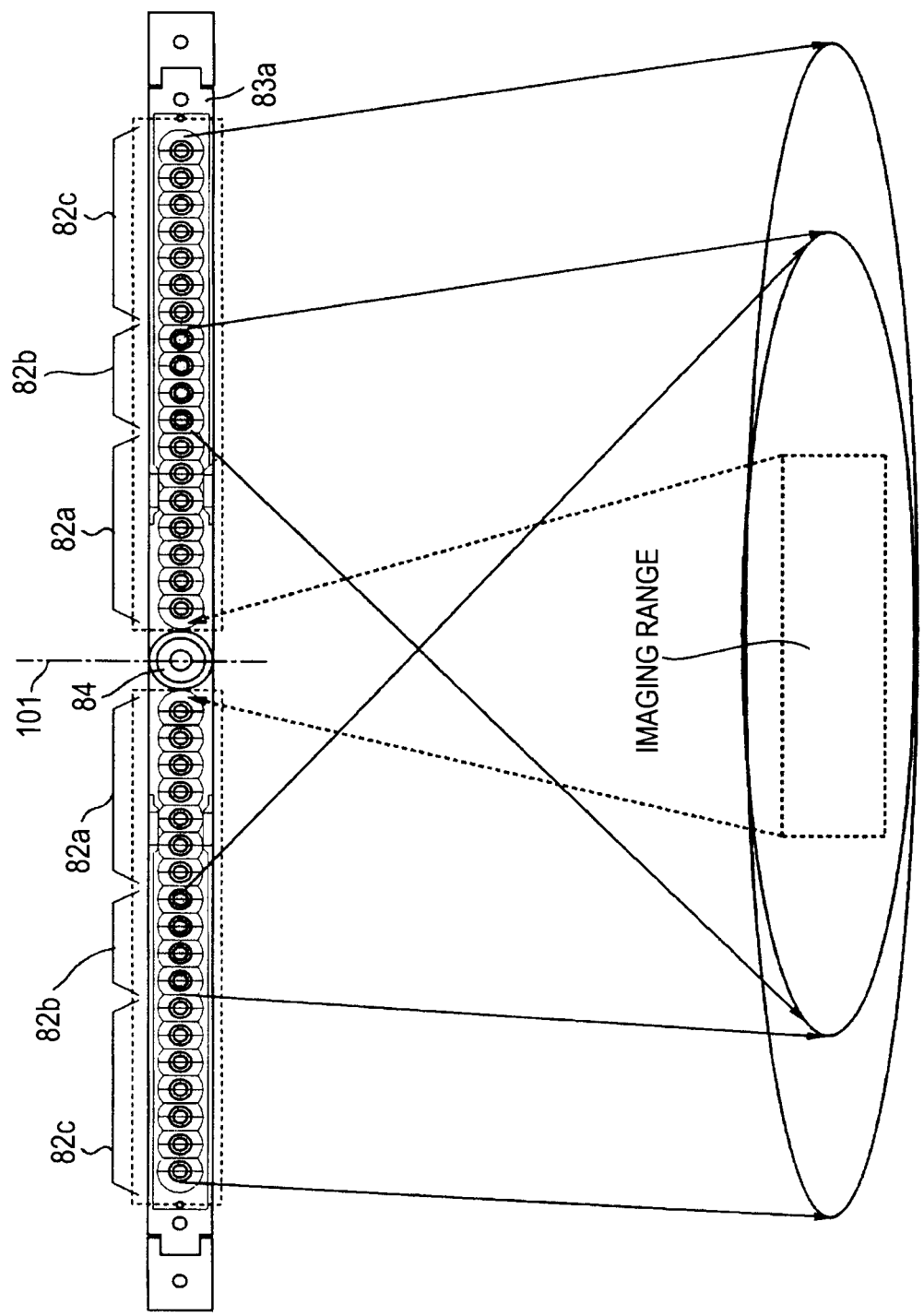
FIG. 7 is an illustration showing illumination provided by light source groups.

FIG. 7 shows an example of a light source group 82 disposed on the light source substrate 83a.

The light source group 82 is disposed on the light source substrate 83a such that the illuminance distribution of illumination light having the wavelength $\lambda 1$ and the illuminance distribution of illumination light having the wavelength $\lambda 2$ coincide with each other within the imaging range shown in FIG. 7.

For example, light source groups (the light source groups 82a and 82c in the case shown in FIG. 7) radiating light having the wavelength $\lambda 1$ and light source groups (the light source groups 82b in the case shown in FIG. 7) radiating light having the wavelength $\lambda 2$ are disposed as the light source group 82 in such positions that the groups are line-symmetric about the axis 101. Each of LEDs forming each of light source groups 82a, 82b, and 82c is disposed in such a position that its radiating direction (the traveling direction of the ray at the center of illumination light rays radiated by the LED in a radial pattern) coincides with the imaging direction of the camera 84 (the direction of the optical axis of the camera 84).

The number of the LEDs radiating the light having the wavelength $\lambda 1$ and the number of the LEDs radiating the light having the wavelength $\lambda 2$ are determined depending on a difference between the degrees of sensitivity that the camera 84 exhibits in receiving the different light rays.

For example, let us assume that the camera 84 exhibits higher sensitivity when receiving the light having the wavelength $\lambda 2$ than when receiving the light having the wavelength $\lambda 1$. Then, the LEDs radiating the light having the wavelength $\lambda 1$ are disposed in a quantity greater than the quantity of the LEDs radiating the light having the wavelength $\lambda 2$ as shown in FIG. 7 such that reflected light rays having the wavelengths $\lambda 1$ and $\lambda 2$ received at the camera 84 can be recognized as having the same intensity.

As shown in FIG. 7, each of the light source groups 82a, 82b, and 82c located on the left side of the axis 101 is formed by a plurality of LEDs. However, each group may be replaced by a single LED. In this case, the light source groups 82a, 82b, and 82c located on the right side of the axis 101 are configured similarly.

For example, in each of the sets of light source groups 82a, 82b, and 82c located on the left and right sides of the axis 101, the light source groups 82a and 82c may be formed by nine LEDs in total, and the light source group 82b may be formed by a single LED.

In the present embodiment, as shown in FIG. 7, the light source groups radiating the light rays having the wavelength $\lambda 1$ and $\lambda 2$ are alternately disposed in such positions that they are line-symmetric about the axis 101. Therefore, the illumination light having the wavelength $\lambda 1$ and the illumination light having the wavelength $\lambda 2$ are evenly radiated to the imaging range. Thus, the illuminance distribution of the illumination light having the wavelength $\lambda 1$ and the illuminance distribution of the illumination light having the wavelength $\lambda 2$ (substantially) coincide with each other.

In the skin recognition module 62, the camera 84 can acquire (generate) first and second images allowing a skin area to be more accurately detected, the higher the degree of coincidence between the illumination distribution of the illumination light having the wavelength $\lambda 1$ and the illuminance distribution of the illumination light having the wavelength $\lambda 2$. Therefore, a skin area can be more accurately detected according to the present embodiment.

In the present embodiment, as shown in FIG. 7, light source groups radiating light having the wavelength $\lambda 1$ and light source groups radiating light having the wavelength $\lambda 2$ are alternately disposed as the light source group 82. In addition, the light source group 82 is disposed such that the radiating directions of the group coincide with the imaging direction of the camera 84. Thus, when compared to an approach involving only the step of disposing light source groups having different wavelengths alternately, the embodiment allows illumination light having the wavelength $\lambda 1$ and the illumination light having the wavelength $\lambda 2$ to be more evenly radiated to the imaging range to achieve a higher level of coincidence between the illuminance distributions of the different light rays.

Further, since the light source groups 82a, 82b, and 82c are disposed on both of the left and right sides of the camera 84 located in the middle as shown in FIG. 7, illumination light for illuminating an object existing in the imaging range of the camera 84 can illuminate the entire object in an unbiased manner (evenly) when compared to illumination provided by disposing the light source groups 82a, 82b, and 82c only on the right or left side of the camera 84 in the middle in FIG. 7.

It is therefore possible to avoid, for example, a situation in which the detection of a skin area representing a hand of a user or the like as an object to be imaged is disabled by shadows on the user's hand or the like produced as a result of insufficient illumination of the user's hand or the like with illumination light.

2. Modifications

In the embodiment of the invention, the light source group 82 is provided near the camera 84 to make the skin recognition module 62 compact. As a result, the camera 84 may directly receive illumination light from LEDs 121 dispose near the same.

In such a case, the camera 84 of the skin recognition module 62 acquires (generates) first and second images imaged by receiving reflected light which is accompanied by illumination light, and the image processing section 85 detects a skin area based on the first and second images imaged by receiving the reflected light accompanied by the illumination light.

However, when a skin area is detected at the skin recognition module 62 based on first and second images imaged by receiving reflected light accompanied by illumination light as thus described, the skin area is detected at accuracy lower than that achieved by detecting the skin area based on first and second images imaged by receiving reflected light only.

Figure 8:
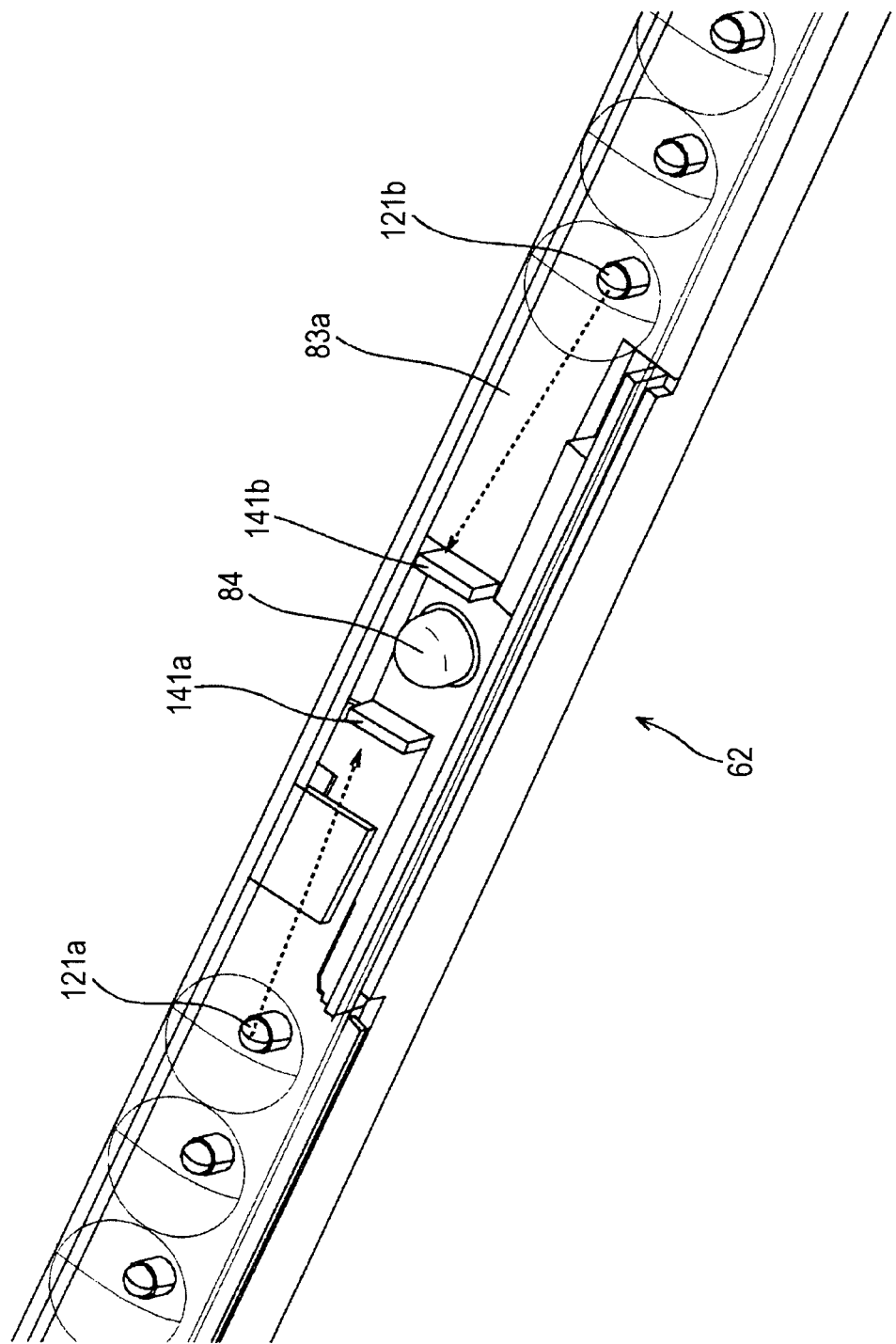
FIG. 8 is an illustration showing an example of a skin recognition module having shield plates.

As a solution to the problem, shield plates 141a and 141b may be provided between the camera 84 and the LEDs 121a and 121b disposed in the vicinity of the camera 84 as shown in FIG. 8 to block illumination light from the LEDs 121a and 121b. As a result, illumination light from the LEDs 121a and 121b can be prevented from impinging on the camera 84 to allow the skin of a person to be recognized based on first and second images imaged by receiving reflected light only. This approach allows a skin area to be more accurately detected when compared to detection performed without the shield plates 141a and 141b.

In the embodiment of the invention, since the LEDs forming the light source group 82 are disposed close to each other to make the skin recognition module 62 compact, the LEDs are likely to undergo a temperature rise attributable to heat generated by the emission of the LEDs themselves. In such a situation, the output of the LEDs may be reduced as a result of the temperature rise at the LEDs forming the light source group 82.

As a solution to the problem, the above-described shield plates 141a and 141b may be formed from a metal having high heat absorption (heat conductivity) to use them as radiating plates for absorbing and radiating heat generated as a result of the emission of the LEDs.

Thus, the temperature rise attributable to heat generated as a result of the emission of the LEDs can be suppressed to prevent the reduction in the output of the LEDs. It is therefore possible to prevent the illuminance distribution of illumination light having the wavelength λ1 and the illuminance distribution of illumination light having the wavelength λ2 from changing into different states of distribution attributable to the suppressed output of the LEDs.

Figure 9:
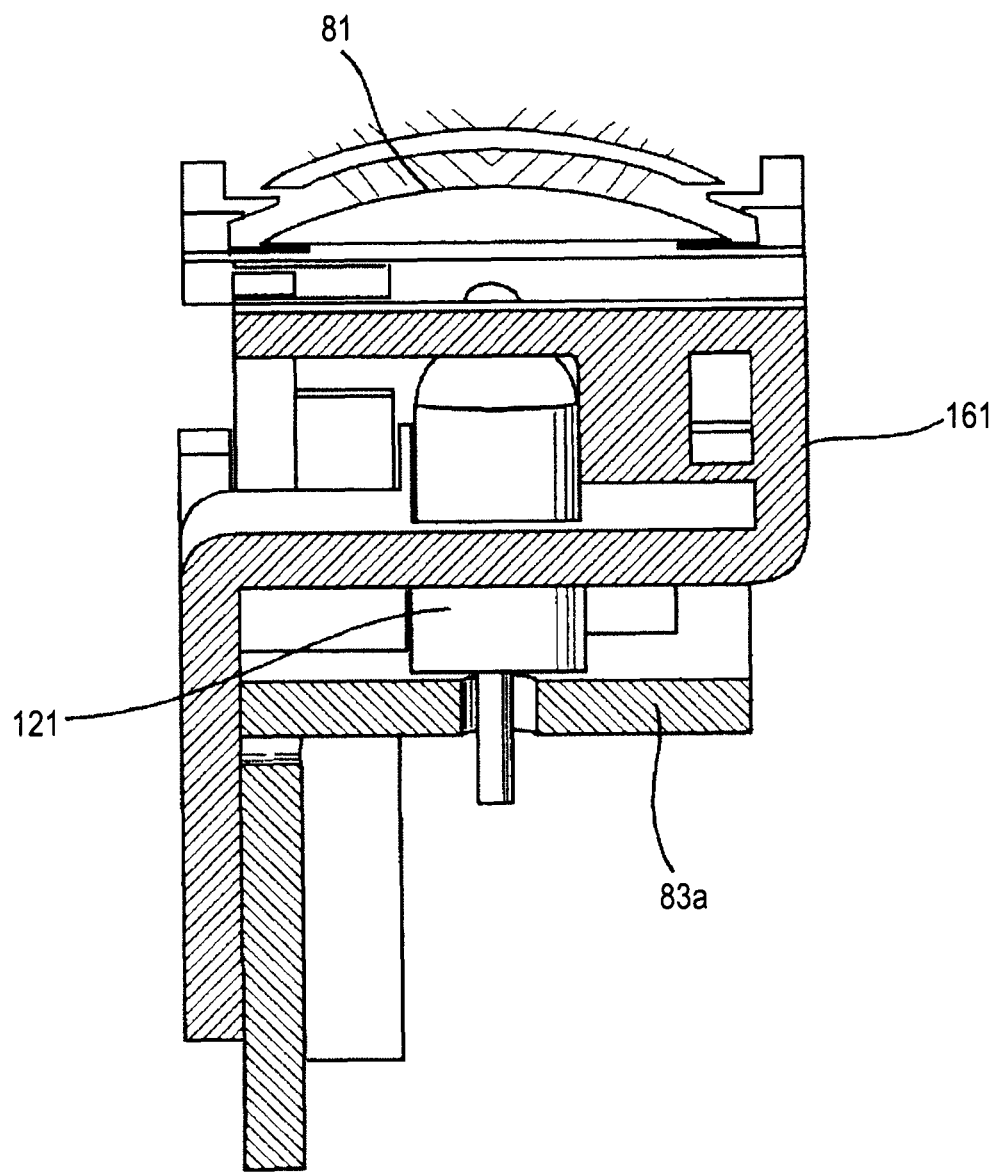
FIG. 9 is an illustration showing an example of a skin recognition module having a sheet metal.

In the modification, for example, a sheet metal 161 fabricated by molding a metal having high heat absorption may be provided in contact with the LEDs 121 as shown in FIG. 9 to allow heat generated at the LEDs 121 to be absorbed and radiated by the sheet metal 161.

In the embodiment of the invention, the LEDs 121 are disposed on the light source substrate 83a to secure the LEDs 121 in such positions that the radiating directions of the LEDs 121 coincide with the imaging direction of the camera 84. Alternatively, the LEDs 121 may be secured to the sheet metal 161 which is fabricated as part of the support member 86. In this case, the radiating directions of the LEDs 121 can be fixed more appropriately in addition to the effect of suppressing a temperature rise attributable to heat generated by the emission of the LEDs 121 to prevent a reduction in the output of the LEDs 121.

Specifically, the radiating directions of the LEDs 121 of the embodiment are determined when the LEDs are disposed on the light source substrate 83a, and errors can occur in the radiating directions of the LEDs 121 when the LEDs 121 are disposed on the light source substrate 83a because of dimensional errors of the light source substrate 83a or the like (errors between designed dimensions and actual dimensions of the light source substrate 83a).

Errors of the radiating directions of the LEDs 121 may be also caused by dimensional errors of the support member 86 or the like when the light source substrate 83a having the LEDs 121 disposed thereon is supported by the support member 86.

On the contrary, for example, when the sheet metal 161 is fabricated as part of the support member 86 to secure the LEDs 121 with the sheet metal 161, errors of the radiating directions of the LEDs 121 can be caused only by dimensional errors of the sheet metal 161 or the like when the LEDs 121 are secured to the sheet metal 161. It is therefore possible to prevent errors of the radiating directions of the LEDs 121 from occurring at two stages of manufacture like those included in the embodiment, i.e., the stage at which the LEDs 121 are disposed on the light source substrate 83a and the stage at which the light source substrate 83a is supported by the support member 86.

When the emitting directions of the LEDs 121 are determined by the sheet metal 161 fabricated as part of the support member 86 as thus described, errors of the emitting directions of the LEDs 121 can be reduced, and heat generated by the LEDs 121 can be efficiently radiated without using a radiating agent or the like.

Figure 10:
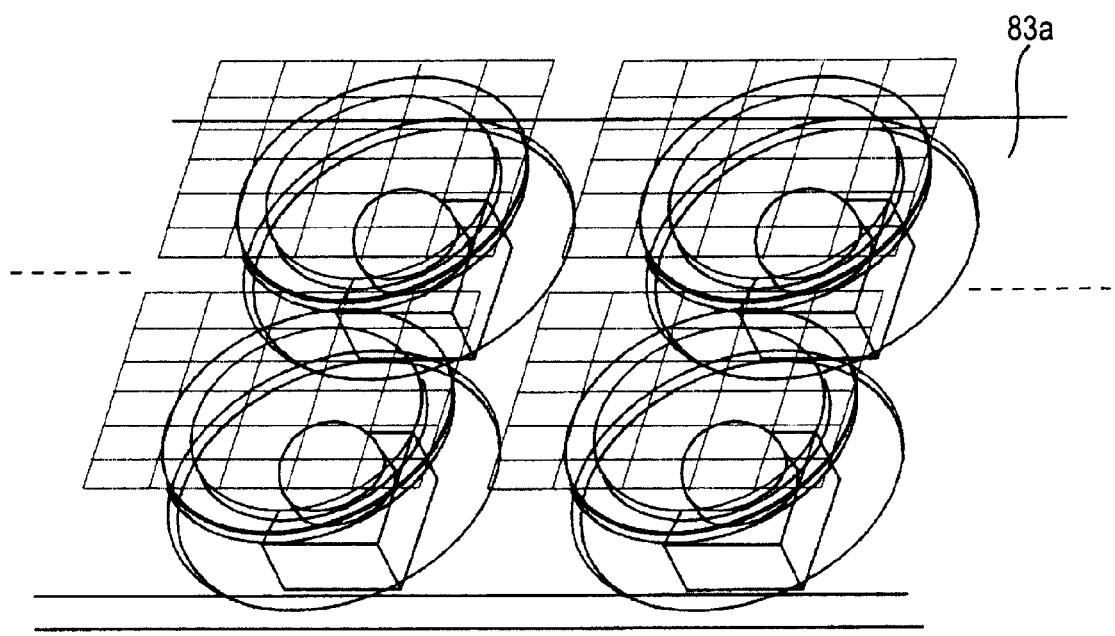
FIG. 10 is an illustration showing an example of disposition of LEDs forming a light source group.

In the embodiment of the invention, the LEDs are disposed in a row on the light source substrate 83a as shown in FIG. 4. Alternatively, the LEDs may be disposed, for example, in two rows as shown in FIG. 10 as long as the LEDs are disposed in such positions that they are line-symmetric about the axis 101.

In the embodiment of the invention, the LEDs forming the light source group 82 are disposed in such positions that the LEDs are line-symmetric about the axis 101 of the camera 84. Alternatively, the LEDs may be disposed, for example, such that they are point-symmetric about the camera.

In the embodiment of the invention, the skin recognition module 62 is incorporated in the television receiver 41. However, the invention is not limited to the incorporation of the skin recognition module 62 in the television receiver 41, and the module may alternatively be incorporated in, for example, a personal computer or the like.

That is, the skin recognition module 62 may be incorporated in any type of electronic apparatus as long as the electronic apparatus performs processes according to results of detection (recognition) carried out by the skin recognition module 62.

In the present specification, the term "system" means a complex unity formed of a plurality of apparatus.

Embodiments of the invention are not limited to those described above and various modification can be made without departing from the spirit and scope of the invention.

The present application contains subject matter related to that disclosed in Japanese Priority Patent Application JP 2009-187048 filed in the Japan Patent Office on Aug. 12, 2009, the entire contents of which is hereby incorporated by reference.

What is claimed is:

1. An image processing device for detecting a skin area representing the skin of a person in an image obtained by imaging an object, comprising:

a first light source configured to emit light having a first wavelength;

a second light source configured to emit light having a second wavelength different from the first wavelength;

an imager configured to image an object illuminated by the light having the first wavelength and image an object illuminated by the light having the second wavelength;

detection circuitry configured to detect a skin area in either a first image obtained by imaging the object illuminated by the light having the first wavelength or a second image obtained by imaging the object illuminated by the light having the second wavelength based on the first image and the second image; and a substrate on which the first and second light sources are disposed integrally with the imager and the detection circuitry in such positions that the light sources are symmetric about the imager, wherein the first and second light sources are disposed on a straight line on the substrate in such positions that they are symmetric about the imager which is located in the middle of the straight line, the first light source includes a plurality of first light sources disposed on a first straight line parallel to the straight line, the second light source includes a plurality of second light sources disposed on a second straight line parallel to the straight line, a number of the plurality of first light sources and a number of the plurality of second light sources are determined based upon a difference between degrees of sensitivity the imager exhibits in receiving the light having the first wavelength and the light having the second wavelength, and the plurality of first light sources and the plurality of second light sources are disposed on the substrate such that an illuminance distribution of the light having the first wavelength coincides with an illuminance distribution of the light having the second wavelength.

2. An image processing device according to claim 1, further comprising a securing section securing the first and second light sources in such positions that an imaging direction of the imager coincides with light emitting directions of the first and second light sources.

3. An image processing device according to claim 2, wherein the securing section is formed from a metal.

4. An image processing device according to claim 3, further comprising a support section supporting the substrate, wherein the securing section forms part of the support section.

5. An image processing device according to claim 1, further comprising a lens provided to allow light rays from the first and second light sources to be radiated into an imaging range of the imager.

6. An image processing device according to claim 5, wherein the lens is a fly-eye lens or diffraction grating.

7. An image processing device according to claim 1, wherein the substrate includes:
   a light source substrate on which the first and second light sources are disposed, and
   a processing substrate on which the imager and the detection circuitry are disposed.

8. An image processing device according to claim 7, wherein the imager is secured to the light source substrate such that the imager penetrates through the light source substrate in the normal direction thereof.

9. An image processing device according to claim 8, wherein the light source substrate is provided with a shield section for blocking light rays from the first and second light sources which otherwise directly impinge on the imager.

10. An image processing device according to claim 9, wherein the shield section is formed from a metal.

11. An image processing device according to claim 7, wherein the first and second light sources are alternately disposed on the light source substrate in such positions that they are symmetric about the imager.

12. An image processing device according to claim 7, wherein the processing substrate is disposed behind the light source substrate.

13. An image processing device according to claim 7, wherein the light source substrate is relatively larger than the processing substrate.

14. An image processing device according the claim 1, wherein
   every first light source of the plurality of first light sources is disposed on the straight line, and
   every second light source of the plurality of second light sources is disposed on the straight line.

15. An electronic apparatus detecting a skin area representing the skin of a person in an image obtained by imaging an object and performing a process depending on the detected skin area, the apparatus comprising:
   a first light source configured to emit light having a first wavelength;
   a second light source configured to emit light having a second wavelength different from the first wavelength;
   an imager configured to image an object illuminated by the light having the first wavelength and image an object illuminated by the light having the second wavelength;
   detection circuitry configured to detect a skin area in either a first image obtained by imaging the object illuminated by the light having the first wavelength or a second image obtained by imaging the object illuminated by the light having the second wavelength based on the first image and the second image;
   a substrate on which the first and second light sources are disposed integrally with the imager and the detection circuitry in such positions that the light emitting sources are symmetric about the imager; and
   processing circuitry configured to perform a process according to the result of the detection performed by the detection circuitry, wherein
   the first and second light sources are disposed on a straight line on the substrate in such positions that they are symmetric about the imager which is located in the middle of the straight line,
   the first light source includes a plurality of first light sources disposed on a first straight line parallel to the straight line,
   the second light source includes a plurality of second light sources disposed on a second straight line parallel to the straight line,
   a number of the plurality of first light sources and a number of the plurality of second light sources are determined based upon a difference between degrees of sensitivity the imager exhibits in receiving the light having the first wavelength and the light having the second wavelength, and
   the plurality of first light sources and the plurality of second light sources are disposed on the substrate such that an illuminance distribution of the light having the first wavelength coincides with an illuminance distribution of the light having the second wavelength.

* * * * *